(12) United States Patent
Tortelli et al.

(10) Patent No.: US 6,835,856 B2
(45) Date of Patent: Dec. 28, 2004

(54) PROCESS FOR PREPARING FLUOROHALOGENETHERS

(75) Inventors: Vito Tortelli, Milan (IT); Pierangelo Calini, Milan (IT)

(73) Assignee: Solvay Solexis S.p.A., Milan (IT)

( * ) Notice: Subject to any disclaimer, the term of this patent is extended or adjusted under 35 U.S.C. 154(b) by 0 days.

(21) Appl. No.: 10/633,565

(22) Filed: Aug. 5, 2003

(65) Prior Publication Data

US 2004/0030146 A1 Feb. 12, 2004

(30) Foreign Application Priority Data

Aug. 6, 2002 (IT) ..................................... MI2002A1782

(51) Int. Cl.⁷ .............................................. C07C 41/06
(52) U.S. Cl. ..................... 568/615; 568/607; 568/663; 568/684
(58) Field of Search ................. 568/607, 615, 568/663, 684

(56) References Cited

U.S. PATENT DOCUMENTS

| | | | |
|---|---|---|---|
| 3,453,333 A | 7/1969 | Litt et al. .................... | 568/684 |
| 4,801,409 A | 1/1989 | Marraccini et al. .......... | 562/825 |
| 4,816,599 A | 3/1989 | Gregorio et al. ............. | 560/300 |
| 4,827,024 A | 5/1989 | Guglielmo et al. .......... | 560/300 |
| 4,900,872 A | 2/1990 | Guglielmo et al. .......... | 568/684 |
| 4,962,282 A | 10/1990 | Marraccini et al. .......... | 562/825 |
| 5,710,345 A * | 1/1998 | Navarrini et al. ............ | 568/596 |

FOREIGN PATENT DOCUMENTS

| | | | |
|---|---|---|---|
| EP | 0 201 871 A | 11/1986 | ............ C07C/43/12 |

OTHER PUBLICATIONS

New Jersey Department of Health and Senior Services, Hazardous Substance Fact Sheet, dichloromethane, Jun. 1998.*

Patent Abstracts of Japan, vol. 005, No. 085 (C–057), Jun. 3, 1981 & JP 56 030935 A Mar. 28, 1981.

Krespan, Carl G., "Fragmentation of Fluorosulfonyldifluoroacetyl Fluoride Induced By Fluoride Ion", Journal of Fluorine Chemistry, 16, 1980, pp. 385–390.

* cited by examiner

Primary Examiner—Rosalynd Keys
(74) Attorney, Agent, or Firm—Arent Fox PLLC

(57) ABSTRACT

A process for preparing (per)fluorohalogenethers having general formula (I):

$$(R)_nC(F)_mOCAF\text{—}CA'F_2 \qquad (I)$$

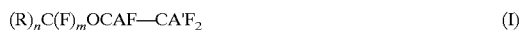

wherein:

A and A', equal to or different the one from the other, are Cl or Br or one is selected from A and A' and hydrogen and the other is halogen selected from Cl, Br; R=F, or a fluorinated, preferably perfluorinated, substituent, selected from the following groups: linear or branched $C_1$–$C_{20}$ alkyl more preferably $C_1$–$C_{10}$; $C_3$–$C_7$ cycloalkyl; aromatic, $C_6$–$C_{10}$ arylalkyl, alkylaryl; $C_5$–$C_{10}$ heterocyclic or alkylheterocyclic; when R is fluorinated or perfluorinated alkyl, cycloalkyl, arylalkyl, alkylaryl, it can optionally contain in the chain one or more oxygen atoms;

when R is fluorinated it can optionally contain one or more H atoms and/or one or more halogen atoms different from F: n is an integer and is 1 or 2; m=3-n; by reaction of carbonyl compounds having formula (II):

$$(R)_pC(F)_q(O) \qquad (II)$$

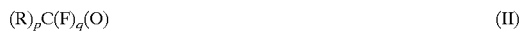

wherein:

p is an integer and is 1 or 2; q is an integer and is zero or 1, R is as above;

in liquid phase with elemental fluorine and with olefinic compounds having formula (III):

$$CAF\text{=}CA'F \qquad (III)$$

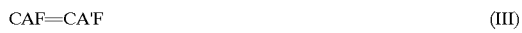

wherein A and A' are as above, at temperatures in the range from –120° C. to –20° C.

12 Claims, No Drawings

PROCESS FOR PREPARING FLUOROHALOGENETHERS

The present invention relates to a process for the preparation of fluorinated vinylethers.

More specifically the present invention refers to the fluorohalogenether preparation which by dehalogenation produce the fluorinated vinylethers. The invention process leads to obtain fluorohalogenethers having improved selectivities.

As known, fluorinated vinylethers are a class of valuable monomers to obtain various polymers, from fluorinated elastomers to thermoprocessable semicrystalline fluorinated polymers.

Processes to obtain fluorohalogenethers based on the reaction of hypofluorites with olefins, are known in the prior art. For the hypofluorite preparation the most known processes use catalysts based on metal fluorides.

In U.S. Pat. No. 4,827,024 it is described the preparation in a continuous way of hypofluorite, by the fluorination reaction in equimolecular amounts with fluorine and halogenated carbonyl compounds having at least two carbon atoms, in the presence of catalysts formed of CsF as such or mixed with metals, such for example copper. Generally said metals are used, besides as catalyst (CsF) supports, also to make easier the thermal exchange, i.e. the dissipation of heat generated in the hypofluorite synthesis.

The metal support according to the above described prior art must satisfy two main functions: 1) to maintain the catalyst in a form accessible to reactants, 2) to make easier the thermal exchange maintaining under control in the required range the catalytic bed temperature. Last but not least a key feature of the support is the complete inertia towards reactants and reaction compounds.

In U.S. Pat. Nos. 4,816,599, 4,801,409 and 4,962,282 hypofluorites are preferably prepared with fluorine in excess to completely convert the acylfluoride into hypofluorite so that the acylfluoride concentration on the catalytic bed be very low, since it is known that some acylfluorides cause decomposition reactions in the presence of CsF. See for example Carl G. Ktrespan in Journal of Fluorine Chemistry, 16 (1980) 385–390.

Tests carried out by the Applicant on the prior art processes for the preparation of hypofluorites using the above catalysts have shown that by using both in a discontinuous and in a continuous way said catalytic systems, the catalytic activity rapidly decreases in the time. The Applicant has found in particular that the activity reduction is very marked, toll to the complete catalyst deactivation, when in the hypofluorite formation reaction the catalyst is used with an excess of fluorine over the stoichiometric value, the latter condition being indicated as preferred in the described prior art processes.

According to the prior art one must therefore operate in excess of fluorine in the hypofluorite synthesis to reduce as much as possible the above inconveniences. By operating under said conditions the catalyst of the prior art deactivates very rapidly, in two-three days. With so short durations it is in practice impossible to have available a continuous industrial plant.

Furthermore in discontinuous hypofluorite synthesis, when the catalytic bed is used in absence of support, its successive reuse in the hypofluorite obtainment reaction leads to very low yields and a very rapid deactivation is observed.

Processes to obtain fluorinated vinylethers are known in the prior art. U.S. Pat. No. 4,900,872 describes the perfluorovinylether precursor preparation, by continuous reaction between perfluoroalkyl hypofluorites diluted in an inert solvent and an olefin having formula CA'F=CA''F, wherein A and A', equal to or different from each other, are Cl and Br. In the patent it is indicated that said hypofluorites can be directly fed from the reactor wherein their synthesis in gaseous phase takes place, by reaction of fluorine with acylfluoride on catalyst. The obtained compounds are converted to perfluorovinylethers by dehalogenation with zinc. In said process the drawbacks are those reported above as to the hypofluorite preparation. In particular the drawback of said processes is due to the fact to have to synthesize and immediately use hypofluorites, which as known are unstable compounds, in particular when the number of carbon atoms of the hypofluorite perfluoroalkyl chain is higher than or equal to 2. Besides, in the hypofluorite synthesis it is known that one must use a catalyst, with the above drawbacks.

The need was therefore felt to have available a process for preparing fluorohalogenethers overcoming the drawbacks of the prior art.

The Applicant has surprisingly and unexpectedly found that by using the process described hereinafter it is possible to solve said technical problem, and therefore to have available a continuous or discontinuous industrial process having a very high selectivity.

An object of the present invention is a process to prepare (per)fluorohalogenethers having general formula (I):

$$(R)_nC(F)_mOCAF—CA'F_2 \qquad (I)$$

wherein:

A and A', equal to or different the one from the other, are Cl or Br or one is selected from A and A' and hydrogen and the other is halogen selected from Cl, Br; R can have the following meanings: F or a fluorinated, preferably perfluorinated, substituent, selected from the following groups: linear or branched $C_1$–$C_{20}$ alkyl more preferably $C_1$–$C_{10}$; $C_3$–$C_7$ cycloalkyl; aromatic, $C_6$–$C_{10}$ arylalkyl, alkylaryl; $C_5$–$C_{10}$ heterocyclic or alkylheterocyclic;

when R is fluorinated or perfluorinated alkyl, cycloalkyl, arylalkyl, alkylaryl it can optionally contain in the chain one or more oxygen atoms;

when R is fluorinated it can optionally contain one or more H atoms and/or one or more halogen atoms different from F;

n is an integer and is 1 or 2;

m is equal to 3-n;

by reaction of carbonyl compounds having formula (II):

$$(R)_pC(F)_q(O) \qquad (II)$$

wherein:

p is an integer and is 1 or 2;

q is an integer and is zero or 1, with the proviso that when p=2, q=0; when p=1, q=1;

R is as above;

in liquid phase with fluorine and with olefinic compounds having formula (III):

$$CAF=CA'F \qquad (III)$$

wherein A and A' are as above, operating at temperatures from –120° C. to –20° C., preferably from –100° C. to –40° C., optionally in the presence of a solvent inert under the reaction conditions.

The fluorine used in the reaction can optionally be diluted with an inert gas such for example nitrogen or helium.

The formula (II) compounds which can be used are acylfluorides such for example $COF_2$, $CF_3COF$, $C_2F_5COF$, $C_3F_7COF$, $C_7F_{15}COF$, $CF_3CF(OCF_3)CF_2CF_2COF$, $CF_3O(CF_2)_2COF$; ketones as hexafluoroacetone, perfluorodiisopropylketone, etc. Acylfluorides are preferred.

The formula (III) compounds are for example 1,2-dichloro-1,2-difluoroethylene (CFC1112), 1,2-dibromo-1,2-difluoroethylene, preferably CFC 1112.

The process according to the present invention is carried out in a single reactor and the reaction can be carried out in a semicontinuous or continuous way.

The semicontinuous process can be for example carried out by feeding gaseous fluorine in the reactor containing the formula (II) carbonyl compounds and the formula (III) olefinic compounds. The molar ratio (II)/(III) can range in a wide range, for example between 0.05 and 10. The fluorine feeding is continued until total olefin conversion. Said condition can be determined when the reaction exothermy is no longer noticed. In fact by carrying out the reaction of compounds (III) and (II) for example at −100° C., as soon as the reaction compounds react with the elemental fluorine, there is exothermy and the temperature increases of about 5°–15° C. Therefore the reaction ends when for example compound (III) has been completely consumed. At this point the reactor temperature comes back to the initial temperature.

In the continuous process the gaseous fluorine and compounds (II), (III) are fed into the reactor, until reaching the steady state. In practice the reactants are fed into the reactor with established flow-rates and the reaction mixture is continuously drawn. The steady state is reached when the concentration of the three reactants and of the reaction compounds in the reactor is equal to the concentration of the reactants and reaction compounds outflowing from the reactor.

The molar ratios among the reactants are not particularly binding for the present invention process, for example the (II)/(III) molar ratio can range from 0.05 to 10 and $F_2$/(III) between 0.05 and 10.

As solvents in the present invention process, compounds which are liquid and inert in the above temperature range can be used. Compounds selected from (per)fluorocarbons, (per)fluoroethers, (per)fluoropolyethers, perfluoroamines, or respective mixtures, can be for example used. The skilled man in the art is able to select from the above classes the compounds to be used as solvents on the basis of their physical properties.

The Applicant has surprisingly and unexpectedly found that the reaction among a formula (II) compound, the formula (III) olefin and elemental fluorine, in the above temperature range, directly produces formula (I) fluorohalogenethers having an improved selectivity. This result is quite surprising and unexpected. Besides in the invention process no catalyst is used, as on the contrary indicated in the prior art for obtaining fluorohalogenethers from the hypofluorite precursor. Therefore the catalyst absence in the invention process notably simplifies the process, particularly on an industrial scale. Indeed the costs of the catalyst regeneration, of its substitution and generally of the management of the plant section comprising the catalytic reactor are very onerous.

The Applicant has found that by using the process of the prior art to obtain fluorohalogenethers by reaction between the olefin and the hypofluorite obtained from the corresponding acylfluoride, a high amount of hypofluorite decomposes. The hypofluorite decomposition reaction increases with its molecular weight; in practice it takes place if the hypofluorite is different from the methyl hypofluorite. See the comparative Examples. With the invention process there is an improved selectivity even when fluorohalogenethers deriving from the formula (II) compounds are prepared, independently from the number of R carbon atoms. In the invention Examples when the compound (II) is acetylfluoride or propionylfluoride the selectivity in the fluorohalogenether is substantially of the same order.

Besides, compared with the prior art processes which use a catalyst to form the hypofluorites, the invention process has a higher productivity since the plant needs no stops for the catalyst regeneration or substitution. In the invention process the plant part concerning the catalyst preparation, the catalytic section running and the catalyst regeneration is therefore eliminated.

The Applicant has found that in the present invention process the decomposition products deriving from compound (II) are negligible. See the Examples.

Furthermore with the present invention process it is also possible to operate at compound (II) low conversions with high selectivity in the fluorohalogenether.

The formula (II) compounds, differently from hypofluorites which are unstable compounds, do not decompose in the reaction environment and can be recovered for example by distillation. When one operates with hypofluorites, this is not possible owing to the dangerousness of the use of said compounds both during the reaction and during the recovery. It is well known that when hypofluorites are used in the reaction they are let completely react without accumulation in the reaction environment.

The following Examples illustrate the invention with non limitative purposes.

EXAMPLE 1

Synthesis of $CF_3$—$CF_2$—$CF_2OCFCl$—$CF_2Cl$ 57 g of CFCl=CFCl (CFC 1112) and 15 g of $CF_3$—$CF_2COF$ (perfluoropropionyl fluoride, PFPF) are introduced in a 50 cc glass reactor equipped with mechanical stirrer and the solution is maintained at the temperature of −100° C.

By means of a bubbling inlet, fluorine is fed diluted with nitrogen (molar ratio fluorine/nitrogen 1:5) for 6.5 hours. During the fluorine feeding period a moderate reaction exothermy is noticed.

The gas outflowing from the reactor are let flow through a trap containing a fluorinated solvent and maintained at −80° C.

At the reaction end the solutions discharged from the reactor and from the trap are analyzed by gaschromatography.

The material reaction balance is 93.6%, calculated on the solution discharged from the reactor and on the compounds in the trap fluorinated liquid, with conversion of the olefin CFC 1112 and of PFPF of 100% and 61.25%, respectively.

The main PFPF reaction compounds are the following:

A) $CF_3$—$CF_2$—$CF_2OCFCl$—$CF_2Cl$ (propyl adduct)
B) $CF_3$—$CF_2$—$CF_2O(CFCl)_3$—$CF_2Cl$ The selectivity is 73% for A and 17% for B) calculated with respect to PFPF.

Parallelly to the main reaction there is also the fluorination reaction of CFC 1112 to $CF_2Cl$—$CF_2Cl$ (CF 114) and fluorodimerization to $CF_2Cl$—$(CFCl)_3$—$CF_2Cl$ (CFC 1112 dimer); the selectivity with respect to CFC 1112 is 40% for each compound.

The olefin molar balance is about 98%.

The solution discharged from the reactor is distilled. The compound A) structure is confirmed by the $^{19}F$-NMR analysis.

EXAMPLE 2 (COMPARATIVE)

Synthesis of $CF_3$—$CF_2$—$CF_2O$—$CFCl$—$CF_2Cl$ According to the Prior Art a) Hypofluorite $CF_3$—$CF_2$—$CF_2$of synthesis according to U.S. Pat. No. 4,827,024

2.7 g Nl/h of fluorine diluted with nitrogen (molar ratio fluorine/nitrogen 1/10) and 2.3 Nl/h of $CF_3$—$CF_2$—COF (PFPF) are fed into a 500 cc tubular metal reactor, filled with CsF catalyst, mixed with copper wires to disperse the reaction heat. The PFPF is converted in hyofluorite $CF_3$—$CF_2$—$CF_2OF$ with a yield of 99.5%.

b) Synthesis of $CF_3-CF_2-CF_2O-CFCl-CF_2Cl$ by reaction between the hypofluorite and CFC 1112 according to U.S. Pat. No. 4,900,872.

The hypofluyorite produced in a) is fed in a CSTR type reactor (continuous stirred tank reactor), containing 121.2 g of $CFCl=CFCl$ (CFC 1112) and 452 g of $CF_2Cl-CF_3$ (CFC 115) as reaction solvent, and maintained at the temperature of $-90°$ C. The reaction is carried out for 4 hours and then the reactor is discharged and the solution is analyzed by gaschromatography.

The reaction mass balance is 84.3% and the selectivity in propyl adduct referred to the PFPF is 48.1%. The solution is distilled and the isolated compound confirms the analytical yield.

The amount by moles of the formed $COF_2$, determined by acidimetric titration of the compound in the gaseous effluents (off gas), which gives an index of the hypofluorite decomposition by β-scission, is equal to 36% of the starting PFPF.

EXAMPLE 3 (COMPARATIVE)
Synthesis of $CF_3-CF_2O-CFCl-CF_2Cl$ (Ethyl Adduct)

a) Hypofluorite Synthesis

One proceeds as in step a) of the Example 2 (comparative), but feeding 2.3 Nl/h $CF_3-COF$ (PFAF) to the catalytic reactor. The yield in hypofluorite $CF_3-CF_2OF$ is 99.6%.

b) Synthesis of $CF_3-CF_2O-CFCl-CF_2Cl$

One proceeds as in step b) of the Example 2 (comparative) but without using any solvent, by feeding into the CSTR reactor 300 g of CFC 1112. The reaction mass balance is 90%.

The solution discharged from the reactor is analyzed by gaschromatography and the yield in ethyl adduct $CF_3-CF_2O-CFCl-CF_2Cl$, calculated with respect to the fed hypofluorite, is 75%. The remaining 25% of the hypofluorite decomposes forming $COF_2$.

The solution is distilled to recover the ethyl adduct. The recovered amount confirms the yield previously calculated by gaschromatography.

EXAMPLE 4
Synthesis of $CF_3-CF_2O-CFCl-CF_2Cl$ 49 g of $CF_3-COF$ (PFAF) and 24.4 g of $CFCl=CFCl$ (CFC 1112) are introduced into the equipment described in the Example 1. The reaction mixture is maintained at the temperature of $-87°$ C., and 1.5 Nl/h of fluorine diluted with nitrogen (molar ratio fluorine/nitrogen 1/5) are fed therein for 129 minutes.

The reaction mass balance is 90.5% with a PFAF conversion of 10%. The gaschromatographic analysis shows that the main product is $CF_3-CF_2O-CFCl-CF_2Cl$ (ethyl adduct) and the selectivity referred to PFAF is 80%. The complement to 100 are by-products.

EXAMPLE 5
Synthesis of $CF_3-(CF_2)_6-CF_2O-CFCl-CF_2Cl$ 19.65 g of $CF_3-OCFCl-CF_2Cl$ as solvent, 23.07 g of $CFCl=C-FCl$ (CFC 1112) and 7.57 g of $CF_3-(CF_2)_6-COF$ are introduced into the equipment described in the Example 1. The reaction mixture is maintained at the temperature of $-55°$ C. and 1.5 Nl/h of fluorine diluted with nitrogen (molar ratio fluorine/nitrogen 1/5) are fed therein for 110 minutes.

The reaction mass balance is 92.2%, the acylfluoride conversion 25%.

The discharged solution is analyzed by gaschromatography and the main product is the ether $CF_3-(CF_2)_6-CF_2O-CFCl-CF_2Cl$ which forms with a selectivity, referred to the starting acylfluoride, of 90%, the complement to 100 being by-products.

The solution is treated with water and the separated organic phase is distilled. The $^{19}F$ NMR and GC MS analyses confirm the compound structure as above indicated.

EXAMPLE 6
Synthesis of $CF_3CF\ (OCF_3)\ CF_2CF_2CF_2O-CFCl-CF_2Cl$

The Example 1 is repeated introducing into the reactor 16.58 g of $CF_3CF(OCF_3)CF_2CF_2COF$ and 48.85 g of $CFCl=CFCl$ (CFC 1112). The reaction mixture is maintained at the temperature of $-81°$ C. and 1.5 Nl/h of fluorine diluted with nitrogen (molar ratio fluorine/nitrogen 1/5) are fed therein. The test is carried out for 264 minutes and the material balance is 93.5% with a starting acylfluoride conversion equal to 41.8%. The discharged solution is analyzed by gaschromatography and the main compounds are the following perfluorohalogenethers:

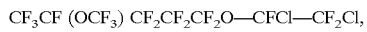

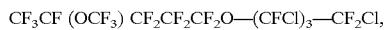

which form with a selectivity, referred to the starting acylfluoride, of 85% and 7.4%, respectively.

The solution is treated with water and from the separated organic phase the ether $CF_3CF_2CF(OCF_3)\ CF_2CF_2O-CFCl-CF_2Cl$ is distilled whose structure is confirmed by $^{19}F$ NMR analysis.

The obtained compound subjected to dechlorination with zinc in dimethyl formamide, at 75° C., provides the corresponding vinylether $CF_3CF_2CF(OCF_3)\ CF_2CF_2O-CF=CF_2$.

EXAMPLE 7
Synthesis of $CF_3O-CFCl-CF_2Cl$

Into the equipment described in the Example 1 maintained at the temperature of $-100°$ C., are introduced 19.2 g of $CF_2Cl-CF_3$.

1.5 Nl/h of fluorine diluted with nitrogen (molar ratio fluorine/nitrogen 1/2.5), 1.5 Nl/h of $CFCl=CFCl$ and 1,5 Nl/h of $COF_2$ are then fed.

The reaction is continued for 2 hours and at the end the reactor is discharged. The reaction mixture is analyzed by gaschromatography.

It is found that the conversion of CFC 1112 is 69.0% and that of $COF_2$ 57.0%.

The reaction mixture is distilled. 12.0 g of a compound having formula $CF_3O-CFCl-CF_2Cl$ ($^{19}F$ NMR) are recovered.

Selectivity with respect to $COF_2$ is 66.7% and with respect to CFC 1112 is 44.6%.

It is found that together with the synthesis of the above compound, also the fluorination raction of CFC 1112 to give CFC 114 and of fluorodimerization to $CF_2Cl-CFCl-CFCl-CF_2Cl$ took place in the reactor.

Selectivity calculated with respect to CFC 1112, for the product CFC 114 is 35.1% and for the CFC 1112 dimer is 7.3%.

The olefin molar balance is 99%.

EXAMPLE 8
Synthesis of $(CF_3)_2-CF-O-CFCl-CF_2Cl$

Into the equipment of the Example 1, maintained at a temperature of $-80°$ C., 16.8 g of $CF_3C(O)CF_3$ are loaded. 1.7 Nl/h of fluorine diluited with nitrogen (molar ratio fluorine/nitrogen 1/2.5) and 1.5 Nl/h di $CFCl=CFCl$ are then fed.

The reaction is continued for 4 hours and at the end the reactor is discharged. The reaction mixture is analyzed by gaschromatography.

It is found that both the conversions of CFC 1112 and of CF$_3$C(O)CF$_3$ are 100%.

The reaction mixture is distilled. 19.5 g of a compound having formula (CF$_3$)$_2$—CF—O—CFCl—CF$_2$Cl ($^{19}$F NMR) are recovered.

Selectivity with respect to CF$_3$C(O)CF$_3$ is 57.0% and with respect to CFC 1112 is of 20.9%.

It is found that together with the synthesis of the above compound, also the fluorination raction of CFC 1112 to give CFC 114 and of fluorodimerization to CF$_2$Cl—CFCl—CFCl—,CF$_2$Cl took place in the reactor.

Selectivity calculated with respect to CFC 1112, for the product CFC 114 is 62.7% and for the CFC 1112 dimer is 1.6%.

The molar balance is 99% for CFC 1112 and 90% for CF$_3$C(O)CF$_3$.

EXAMPLE 9

Synthesis of CF$_3$—CF$_2$—CF$_2$—O—CHF—CF$_2$Cl

Into the equipment of the Example 1, maintained at a temperature of −90° C., 70.0 g of CF$_3$CF$_2$COF and 11.3 g di CHF=CFCl (CFC 1122a) are loaded. 1.5 Nl/h of fluorine diluited with nitrogen (molar ratio fluorine/nitrogen 1/4) are then fed.

The reaction is continued for 1.5 hours and at the end the reactor is discharged. The reaction mixture is analyzed by gaschromatography.

It is found that the conversion of CFC 1122a is 100% and that of CF$_3$CF$_2$COF 20.5%.

1.2 g of CF$_3$—CF$_2$—CF$_2$—O—CHF—CF$_2$Cl are recovered. Selectivity with respect to CF$_3$CF$_2$COF is 4.4% and with respect to CFC 1122a is 3.4%.

It is found that together with the synthesis of the above compound, also the fluorination raction of CFC 1122a to give CFC 124a and of fluorodimerization to CF$_2$Cl—CFH—CFCl—CF$_2$H and isomers thereof CF$_2$Cl—CFH—CFH—CF$_2$Cl and CF$_2$H—CFCl—CFCl—CF$_2$H.

Selectivity, calculated with respect to CFC 1122a, for CFC 124a is 39.4% and for CFC 1122a dimers is 13.6%.

What is claimed is:

1. A process for the preparation of (per) fluorohalogenethers having general formula (I):

(R)$_n$C(F)$_m$OCAF—CA'F$_2$ (I)

wherein:

A and A', equal to or different the one from the other, are Cl or Br or one is selected from A and A' and hydrogen and the other is halogen selected from Cl, Br;

R=F or a fluorinated substituent, selected from: linear or branched C$_1$–C$_{20}$ alkyl; C$_3$–C$_7$ cycloalkyl; aromatic, C$_6$–C$_{10}$ arylalkyl, alkylaryl; C$_5$–C$_{10}$ heterocyclic or alkylheterocyclic;

when R is fluorinated or perfluorinated alkyl, cycloalkyl, arylalkyl, alkylaryl, it can optionally contain in the chain one or more oxygen atoms;

when R is fluorinated it can optionally contain one or more H atoms and/or one or more halogen atoms different from F;

n is an integer and is 1 or 2;

m=3−n;

by reaction of carbonyl compounds having formula (II):

(R)$_p$C(F)$_q$(O) (II)

wherein:

p is an integer and is 1 or 2;

q is an integer and is zero or 1, with the proviso that when p=2, q=0; when p=1, q=1;

R is as above;

in liquid phase with elemental fluorine and with olefinic compounds having formula (III):

CAF=CA'F (III)

wherein A and A' are as above, operating at temperatures from −120° C. to −20° C., optionally in the presence of a solvent inert under the reaction conditions.

2. A process according to claim 1, wherein the fluorine used in the reaction is diluted with an inert gas.

3. A process according to claim 1, wherein the formula (II) compounds are acylfluorides selected from COF$_2$, CF$_3$COF, C$_2$F$_5$COF, C$_3$F$_7$COF, C$_7$F$_{15}$COF, CF$_3$CF(OCF$_3$)CF$_2$CF$_2$COF, CF$_3$O(CF$_2$)$_2$COF; or ketones selected between hexafluoro-acetone, perfluorodiisopropylketone.

4. A process according to claim 1, wherein the formula (II) compounds are acylfluorides.

5. A process according to claim 1, wherein the formula (III) compounds are selected from 1,2-dichloro-1,2-difluoroethylene (CFC 1112), 1,2-dibromo-1,2-difluoro-ethylene.

6. A process according to claim 1, wherein the reaction can be carried out in a semicontinuous or continuous way.

7. A process according to claim 6, wherein in the semicontinuous process the molar ratio between the carbonyl compound (II) and the olefin (III) ranges from 0.05 to 10.

8. A process according to claim 6, wherein in the continuous process the molar ratio between the carbonyl compound (II) and the olefin (III) ranges from 0.05 to 10, the molar ratio fluorine/olefin (III) ranges from 0.05 to 10.

9. The process according to claim 1, wherein R=a perfluorinated, substituent.

10. The process according to claim 1, wherein R is a linear or branched C1–C$_{10}$ alkyl.

11. The process according to claim 1, wherein the temperatures are from −100° C. to −40° C.

12. The process according to claim 5, wherein the formula (III) compound is CFC 1112.

* * * * *